(12) United States Patent
Stoval, III et al.

(10) Patent No.: US 10,685,745 B2
(45) Date of Patent: Jun. 16, 2020

(54) AUTOMATED MEDICAL CASE ROUTING BASED ON DISCREPANCIES BETWEEN HUMAN AND MACHINE DIAGNOSES

(71) Applicant: INTERNATIONAL BUSINESS MACHINES CORPORATION, Armonk, NY (US)

(72) Inventors: William Murray Stoval, III, Acton, MA (US); Marwan Sati, Mississauga (CA); Andjela Azabagic, Cambridge, MA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 6 days.

(21) Appl. No.: 15/844,263

(22) Filed: Dec. 15, 2017

(65) Prior Publication Data
US 2019/0189265 A1    Jun. 20, 2019

(51) Int. Cl.
*G06K 9/00* (2006.01)
*G16H 30/20* (2018.01)
(Continued)

(52) U.S. Cl.
CPC .......... *G16H 30/20* (2018.01); *A61B 5/7264* (2013.01); *G16H 30/40* (2018.01); *G16H 50/70* (2018.01);
(Continued)

(58) Field of Classification Search
CPC ........ G16H 30/20; G16H 50/70; G16H 30/40; G16H 10/60; G16H 50/20; A61B 5/0035; A61B 6/502; A61B 6/5205; G06T 7/0012
See application file for complete search history.

(56) References Cited

U.S. PATENT DOCUMENTS

2007/0133852 A1   6/2007  Collins et al.
2008/0033253 A1   2/2008  Neville et al.
(Continued)

OTHER PUBLICATIONS

Non-Final Office Action from the U.S. Patent and Trademark Office for U.S. Appl. No. 15/844,254 dated Apr. 16, 2019 (19 pages).
(Continued)

*Primary Examiner* — Xin Jia
(74) *Attorney, Agent, or Firm* — Michael Best & Friedrich LLP

(57) ABSTRACT

Methods and systems for verifying a manually-generated report for a medical image. One system comprises an electronic processor configured to receive a first report for the medical image generated by a first radiologist, receive a second report for the medical image generated by a cognitive system, and automatically compare the first report and the second report to detect a discrepancy between the first report and the second report. The electronic processor is also configured to, in response to not detecting a discrepancy between the first report and the second report, submitting the first report for the medical image. The electronic processor is also configured to, in response to detecting a discrepancy between the first report and the second report, assign the medical image to a second radiologist, receive a third report for the medical image generated by the second radiologist, and submit the third report for the medical image.

17 Claims, 7 Drawing Sheets

(51) Int. Cl.
*G16H 30/40* (2018.01)
*G16H 50/70* (2018.01)
*A61B 5/00* (2006.01)
*A61B 6/00* (2006.01)
*G06T 7/00* (2017.01)
*G16H 10/60* (2018.01)
*G16H 50/20* (2018.01)
*A61B 5/055* (2006.01)

(52) U.S. Cl.
CPC ............ *A61B 5/0035* (2013.01); *A61B 5/055* (2013.01); *A61B 6/502* (2013.01); *A61B 6/5205* (2013.01); *G06T 7/0012* (2013.01); *G16H 10/60* (2018.01); *G16H 50/20* (2018.01)

(56) References Cited

U.S. PATENT DOCUMENTS

2016/0364862 A1* 12/2016 Reicher .................. G06F 19/00
2017/0200268 A1* 7/2017 Podilchuk ............ G06K 9/6232
2018/0060512 A1* 3/2018 Sorenson ................ G06F 19/00

OTHER PUBLICATIONS

Non-Final Office Action from the U.S. Patent and Trademark Office for U.S. Appl. No. 15/844,280 dated Dec. 4, 2019 (14 pages).
Non-Final Office Action from the U.S. Patent and Trademark Office for U.S. Appl. No. 15/844,266 dated Dec. 9, 2019 (16 pages).
Non-Final Office Action from the U.S. Patent and Trademark Office for U.S. Appl. No. 15/844,271 dated Dec. 6, 2019 (19 pages).
Non-Final Office Action from the U.S. Patent and Trademark Office for U.S. Appl. No. 15/844,254 dated Jan. 13, 2020 (20 pages).
Non-Final Office Action from the U.S. Patent and Trademark Office for U.S. Appl. No. 15/844,254 dated Nov. 20, 2019 (16 pages).
Final Office Action from the U.S. Patent and Trademark Office for U.S. Appl. No. 15/844,254 dated Mar. 9, 2020 (18 pages).

* cited by examiner

AUTOMATED MEDICAL CASE ROUTING BASED ON DISCREPANCIES BETWEEN HUMAN AND MACHINE DIAGNOSES

FIELD

Embodiments described herein relate to automating patient triage to, among other things, provide quicker and more efficient allocation of medical resources.

SUMMARY

A Picture Archiving and Communication System (PACS) is a central repository for medical image studies. Each image study includes one or more images generated using one or more types of imaging modalities (for example, sonogram, ultrasound, x-ray, magnetic resonance imaging (MM), and the like). The PACS (a server included in the PACS) controls what systems can access stored medical images. A PACS viewer provides a user interface for accessing and viewing stored medical images. The viewer may provide various viewing options based on the type of images being viewed. The viewer may also include a dictation and speech-to-text mechanism that that captures audio input data from a user and converts the audio input data to text data. The PACS may store the text data, transmit the text data to other systems (for example, a hospital system), or a combination thereof. For example, the text data may be inserted into a structured report generated for an image study that includes a radiologist's evaluations and conclusions of the image study.

Workflows (defined organization structures) may be used to track image studies that a user (for example, a radiologist) is interested in reviewing and analyzing. In response to a radiologist selecting an image study from the worklist, a PACS viewer may display one or more of the images included in the selected image study. In some embodiments, the image study worklist is separate from the viewer, which allows a single worklist to communicate with multiple viewers. For example, particular viewers may be customized for particular types of images or radiologists may have particular preferences for certain viewers and the functionality provided through the viewer.

When a radiologist reviews an imaging study, the radiologist manually classifies the patient's case or condition. The radiologist may use one or more known classification systems, such as the BI-RADS classification system, to perform this classification. Upon making such a classification, the radiologist (or other physicians or caretakers, such as the ordering physician) may recommend or order one or more follow-up treatments (including follow-up diagnostic imaging, biopsy procedures, pharmaceuticals, therapy, counseling, office visits, and the like) with the patient. These recommendations may be submitted as correspondence (emails) or may require that the radiologist (or the ordering physician) manually access another system, such as a hospital information system to manually schedule a follow-up treatment.

The above manual review and evaluation process has numerous deficiencies. For example, the number of medical images obtained worldwide continues to rapidly grow due to enhancements in imaging technology, including MRI, spiral computed tomography (CT), position emission tomography (PT), ultrasound, various forms of radiography, mammography, breast tomosynthesis, medical photography and mobile imaging applications. The number of images generated using these and other technologies surpass the capacity of expert physicians (radiologists) to quickly and effectively analyze each image. For example, a CT scan of an abdomen that once included 100 or fewer images now commonly includes 1,000 to 3,000 images. A physician who reports 50 CTs, MRIs, or PT scans in a day may now be required to view and analyze approximately 100,000 medical images from the current exams in addition to relevant prior exams for comparison. Also, there is now more clinical data from more sources that must also be integrated with imaging information.

Furthermore, the delay associated with the above manual processes can delay a patient diagnosis, which may lead to health concerns and patient stress, and can waste medical resources. For example, women are typically screened for breast cancer through a two-stage screening process. During an initial screening process, an image study, such as an x-ray study, is performed. A radiologist manually reviews the image studies from these initial screenings and classifies or triages the initial screenings to identify those patients having normal breast tissue and those patients considered high risk where additional screening is recommended. Accordingly, based on the manual classification of the radiologist, a subset of women participating in the initial screening are asked to return for a second look or second diagnostic imaging, such as diagnostic X-ray mammography, second look ultrasound, MRI, or the like. Also, following such additional diagnostic imaging, a biopsy may be ordered if a suspicious lesion is detected. Thus, when a women needs to return for a second visit, the woman must schedule another imaging procedure, which is inconvenient for the woman and also delays the woman's ultimate diagnosis and any treatment that could aid the woman's diagnosis. The manual review can also lead to fatigue given the large volume of screening patients per radiologist.

Accordingly, the manual review process introduces delays and potentially errors into triaging patients and, therefore, there is an ever-growing need to increase the speed and accuracy of medical image review.

To address these and other deficiencies with existing image study review systems and methods, embodiments described herein provide automated methods and systems for triaging patients based on cognitive classification of medical images. Based on the triage of the patient and the classification of the patient's medical images, the systems and methods automatically generate worklists for high priority cases and may reserve medical resources, such as via one or more external systems. For lower priority cases, the systems and methods may automatically generate reports for the image studies, which may be reviewed and approved by radiologists. In some embodiments, the methods and systems also perform a differential diagnosis, which provides a set of possible diagnoses and their associated probabilities.

In particular, embodiments described herein invention provide a system for automatically triaging an image study of a patient generated as part of a medical imaging procedure. The system includes a computing device including an electronic processor. The electronic processor is configured to submit at least a portion of the image study to a cognitive system, the cognitive system configured to analyze the image study using a model developed using machine learning, receive, from the cognitive system, a BI-RADS classification assigned to the image study using the model, and automatically triage the image study based on the classification assigned to the image study by the cognitive system.

Another embodiment provides non-transitory computer-readable medium including instructions that, when executed by an electronic processor, perform a set of functions. The set of functions includes submitting least a portion of a first image study of a patient generated as part of a medical imaging procedure to a cognitive system, the cognitive system configured to analyze the first image study using a model developed using machine learning, receiving, from the cognitive system, a BI-RADS classification assigned to the first image study using the model, and comparing an image included in the first image study to an image included in a second image study of the patient to determine a patient change, the second image study generated prior to the first image study. The set of functions also includes receiving a BI-RADS classification assigned to a third image study of the patient, the third image study generated by a different imaging modality than the first image study, and automatically triaging the first image study based on the BI-RADS classification assigned to the first image study by the cognitive system, the patient change, and the BI-RADS classification assigned to the third image study.

A further embodiment provides a method of automatically analyzing an image study of a patient generated as part of a medical imaging procedure. The method includes receiving, with an electronic processor, a first BI-RADS classification for the image study, the first BI-RADS classification manually provided by a radiologist, submitting, with the electronic processor, at least a portion of the image study to a cognitive system, the cognitive system configured to analyze the image study using a model developed using machine learning, and receiving, with the electronic processor, a second BI-RADS classification for the image study, the second BI-RADS classification assigned by the cognitive system using the model. The method also includes comparing, with the electronic processor, the first BI-RADS classification and the second BI-RADS classification to determine whether the first BI-RADS classification and the second BI-RADS classification differs, and, in response to the first BI-RADS classification and the second BI-RADS classification differing, generating an alert for the radiologist and prompting the radiologist to confirm the first BI-RADS classification. The method further includes receiving input from the radiologist in response to the prompt, the input confirming the first BI-RADS classification, and, in response to receiving the input, providing the first BI-RADS classification to the cognitive system as feedback for updating the model using machine learning.

Another embodiment provides a system for automatically triaging an image study of a patient generated as part of a medical imaging procedure. The system includes a computing device including an electronic processor. The electronic processor is configured to receive, from a cognitive system applying a model developed using computer vision and machine learning techniques based on deep learning methodology to classify image studies, a classification assigned to the image study using the model, and automatically generating a worklist based on the classification assigned to the image study using the model, the worklist prioritizing a plurality of tasks for treating the patient.

Other embodiments provide non-transitory computer-readable medium including instructions that, when executed by an electronic processor, perform a set of functions. The set of functions including receiving, from a cognitive system applying a model developed using computer vision and machine learning techniques based on deep learning methodology to classify image studies, a classification assigned to the image study using the model, comparing an image included in the first image study to an image included in a second image study of the patient to determine a patient change, the second image study generated prior to the first image study, and receiving a classification assigned to a third image study of the patient, the third image study generated by a different imaging modality than the first image study. The set of functions further includes automatically generating a worklist for the first image study based on the classification assigned to the first image study using the model, the patient change, and the classification assigned to the third image study, the worklist prioritizing a plurality of tasks for treating the patient.

Further embodiments provide a method of automatically analyzing an image study of a patient generated as part of a medical imaging procedure. The method includes receiving, with an electronic processor, a classification from a cognitive system, the cognitive system applying a model developed using computer vision and machine learning techniques based on deep learning methodology to classify image studies based on a classification schema, automatically generating, with the electronic processor, a worklist based on the classification assigned to the image study using the model, the worklist prioritizing a plurality of tasks for treating the patient; and automatically routing, with the electronic processor, the image study to a radiologist based on the worklist and the classification.

Further embodiments provide a system for automatically triaging an image study of a patient generated as part of a medical imaging procedure. The system includes a computing device including an electronic processor. The electronic processor is configured to receive, from a cognitive system applying a model developed using computer vision and machine learning techniques based on deep learning methodology to classify image studies, a classification assigned to the image study using the model, and automatically communicate with a resource allocation system to reserve at least one medical resource for treating the patient based on the classification assigned by the model.

Embodiments described herein also provide mon-transitory computer-readable medium including instructions that, when executed by an electronic processor, perform a set of functions. The set of functions including receiving, from a cognitive system applying a model developed using computer vision and machine learning techniques based on deep learning methodology to classify image studies, a classification assigned to the image study using the model, comparing an image included in the first image study to an image included in a second image study of the patient to determine a patient change, the second image study generated prior to the first image study, and receiving a classification assigned to a third image study of the patient, the third image study generated by a different imaging modality than the first image study. The electronic processor is also configured to automatically communicating with a resource allocation system to reserve at least one medical resource for treating the patient based on the classification assigned to the first image study using the model, the patient change, and the classification assigned to the third image study.

A further embodiment provides a method of automatically analyzing an image study of a patient generated as part of a medical imaging procedure. The method includes receiving, with an electronic processor, a classification from a cognitive system, the cognitive system applying a model developed using computer vision and machine learning techniques based on deep learning methodology to classify image studies based on a classification schema, automatically, with the electronic processor, generating a worklist based on the classification assigned by the model, the worklist prioritizing a plurality of tasks for treating the patient, and automatically, with the electronic processor, communicating with a resource allocation system to reserve at least one medical resource for treating the patient based on the classification assigned to the image study using the model and at least one of the plurality of tasks included in the worklist.

Embodiments described herein also provide a system for automatically triaging an image study of a patient generated as part of a medical imaging procedure. The system includes a computing device including an electronic processor. The electronic processor is configured to receive, from a cognitive system applying a model developed using computer vision and machine learning techniques based on deep learning methodology to classify image studies, a classification assigned to the image study using the model, and automatically generate a structured report for the image study based on the classification assigned by the model, the structured report accessible by a radiologist via a structured reporting system.

Other embodiments provide non-transitory computer-readable medium including instructions that, when executed by an electronic processor, perform a set of functions. The set of functions including receiving, from a cognitive system applying a model developed using computer vision and machine learning techniques based on deep learning methodology to classify image studies, a classification assigned to the image study using the model, comparing an image included in the first image study to an image included in a second image study of the patient to determine a patient change, the second image study generated prior to the first image study, and receiving a classification assigned to a third image study of the patient, the third image study generated by a different imaging modality than the first image study. The set of functions further including automatically generating a structured report for the image study based on the classification assigned to the first image study using the model, the patient change, and the classification assigned to the third image study.

Another embodiment provides a method of automatically analyzing an image study of a patient generated as part of a medical imaging procedure. The method includes receiving, with an electronic processor, a classification from a cognitive system for the image study, the cognitive system applying a model developed using computer vision and machine learning techniques based on deep learning methodology to classify image studies based on a classification schema, automatically, with the electronic processor, generating a structured report for the image study based on the classification assigned by the model, and automatically, with the electronic processor, populating at least one field included in the structured report based on the classification assigned by the model. The method further includes submitting, with the electronic processor, the structured report to a radiologist for review and approval.

Additional embodiments provide a system for automatically triaging an image study of a patient generated as part of a medical imaging procedure. The system comprising a computing device including an electronic processor. The electronic processor is configured to receive, from a cognitive system applying a model developed using computer vision and machine learning techniques based on deep learning methodology to classify image studies, a classification assigned to the image study using the model, automatically generate a differential diagnosis for the patient based on the classification assigned by the model, and automatically adjust triaging of the image study based on the differential diagnosis.

Further embodiments provides non-transitory computer-readable medium including instructions that, when executed by an electronic processor, perform a set of functions. The set of functions including receiving, from a cognitive system applying a model developed using computer vision and machine learning techniques based on deep learning methodology to classify image studies, a classification assigned to the image study using the model, automatically generating a differential diagnosis for the patient based on the classification assigned by the model, and automatically adjusting triaging of the image study based on the differential diagnosis.

Yet another embodiment provides a method of automatically analyzing an image study of a patient generated as part of a medical imaging procedure. The method includes receiving, with an electronic processor, a classification from a cognitive system for the image study, the cognitive system applying a model developed using computer vision and machine learning techniques based on deep learning methodology to classify image studies based on a classification schema, automatically, with the electronic processor, generating a differential diagnosis for the patient based on the classification assigned by the model and data accessible via an electronic medical record of the patient, and automatically adjusting triaging of the image study based on the differential diagnosis.

Embodiments described herein also provide a system for verifying a manually-generated report for a medical image. The system comprises an electronic processor configured to receive a first report for the medical image generated by a first radiologist, receive a second report for the medical image generated by a cognitive system, and automatically compare the first report and the second report to detect a discrepancy between the first report and the second report. The electronic processor is also configured to, in response to not detecting a discrepancy between the first report and the second report, submitting the first report for the medical image. The electronic processor is also configured to, in response to detecting a discrepancy between the first report and the second report, assign the medical image to a second radiologist, receive a third report for the medical image generated by the second radiologist, and submit the third report for the medical image.

Embodiments also provide a method for verifying a manually-generated report for a medical image. The method includes receiving, with an electronic processor, a first report for the medical image generated by a first radiologist, receiving, with the electronic processor, a second report for the medical image generated by a cognitive system, wherein the first report is generated without access to the second report, and automatically, with the electronic processor, comparing the first report and the second report to detect a discrepancy between the first report and the second report. The method also includes, in response to not detecting a discrepancy between the first report and the second report, automatically submitting, with the electronic processor, the first report for the medical image. In addition, the method includes, in response to detecting a discrepancy between the first report and the second report, assigning the medical image to a second radiologist, receiving a third report for the medical image generated by the second radiologist, and submitting the third report for the medical image.

Yet further embodiments provides non-transitory computer readable medium storing instructions that, when executed by an electronic processor, perform a set of functions. The set of functions including receiving a first report for the medical image generated by a first radiologist, receiving a second report for the medical image generated by a cognitive system, wherein the first report is generated without access to the second report, and automatically comparing the first report and the second report to detect a discrepancy between the first report and the second report. The set of functions also including, in response to not detecting a discrepancy between the first report and the second report, automatically submitting at least one of the first report and the second report for the medical image. In addition, the set of functions includes, in response to detecting a discrepancy between the first report and the second report, assigning the medical image to a second radiologist for completion of a third report without access to the first report and the second report, receiving a third report for the medical image generated by the second radiologist, and submitting at least one of the first report, the second report, and the third report for the medical image.

Other aspects of the invention will become apparent by consideration of the detailed description and accompanying drawings.

DETAILED DESCRIPTION

Before embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or couplings, whether direct or indirect. Also, electronic communications and notifications may be performed using any known means including direct connections, wireless connections, etc.

A plurality of hardware and software based devices, as well as a plurality of different structural components may be utilized to implement the invention. In addition, embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the invention may be implemented in software (for example, stored on non-transitory computer-readable medium) executable by one or more processors. As such, it should be noted that a plurality of hardware and software based devices, as well as a plurality of different structural components, may be utilized to implement the invention. For example, "mobile device," "computing device," and "server" as described in the specification may include one or more electronic processors, one or more memory modules including non-transitory computer-readable medium, one or more input/output interfaces, and various connections (for example, a system bus) connecting the components.

Figure 1:
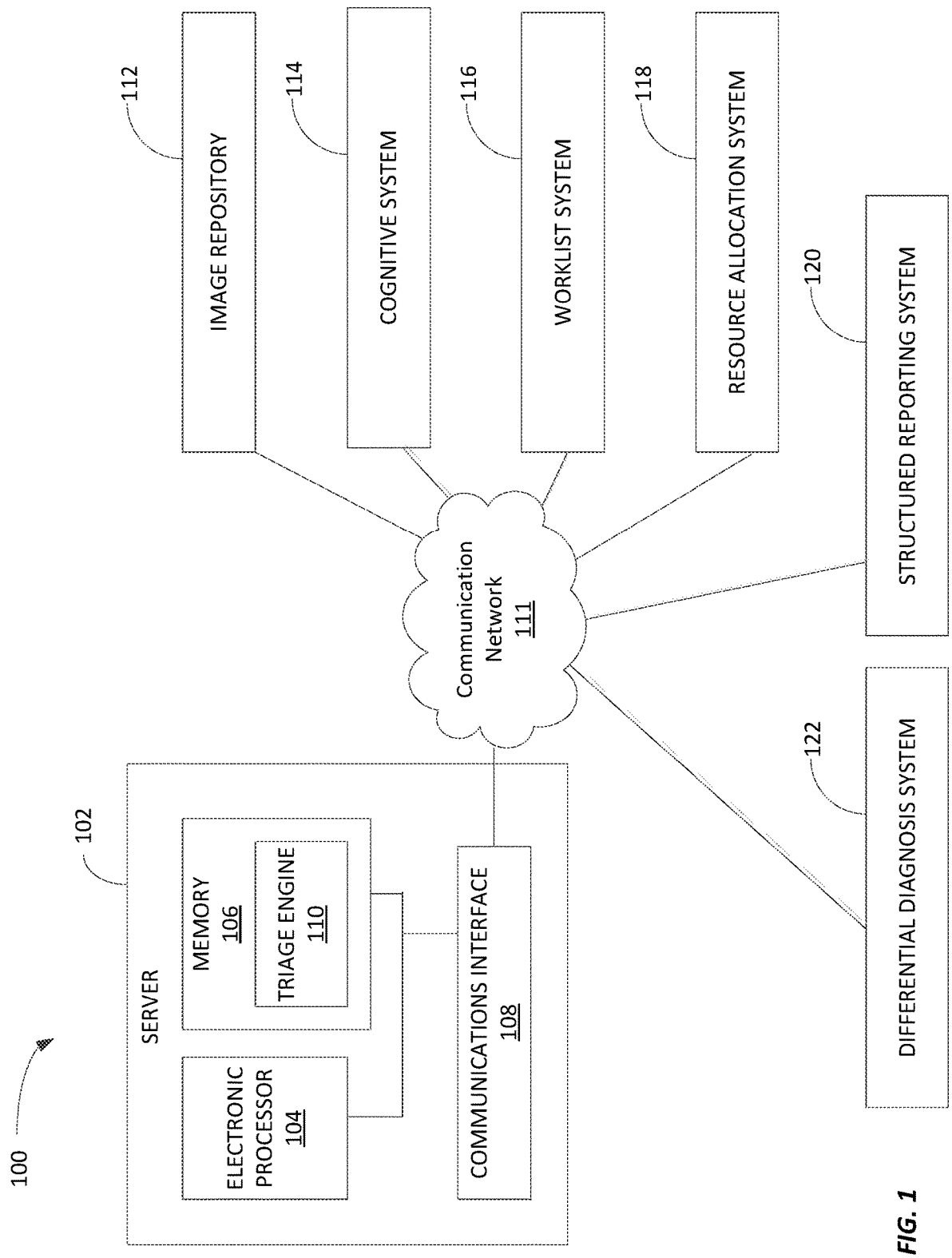
FIG. 1 illustrates a system for automatically triaging image studies according to some embodiments.

FIG. 1 illustrates a system 100 for automatically triaging patients according to some embodiments of the invention. The system 100 includes a server 102 that includes a plurality of electrical and electronic components that provide power, operational control, and protection of the components within the server 102. For example, as illustrated in FIG. 1, the server 102 includes an electronic processor 104 (a microprocessor, application-specific integrated circuit (ASIC), or another suitable electronic device), a memory 106 (a non-transitory, computer-readable storage medium), and a communications interface 108. The electronic processor 104, the memory 106, and the communications interface 108 communicate over one or more connections or buses. It should be understood that the server 102 illustrated in FIG. 1 represents one example of a server and embodiments described herein may include a server with additional, fewer, or different components than the server 102 illustrated in FIG. 1. Also, in some embodiments, the server 102 performs functionality in addition to the functionality described herein. Similarly, the functionality performed by the server 102 (through execution of instructions by the electronic processor 104) may be distributed among multiple servers (including servers included a cloud-based computing system or service). Accordingly, functionality described herein as being performed by the electronic processor 104 may be performed by one or more electronic processors included in the server 102, external to the server 102, or a combination thereof.

The memory 106 may include read-only memory (ROM), random access memory (RAM) (for example, dynamic RAM (DRAM), synchronous DRAM (SDRAM), and the like), electrically erasable programmable read-only memory (EEPROM), flash memory, a hard disk, a secure digital (SD) card, other suitable memory devices, or a combination thereof. The electronic processor 104 executes computer-readable instructions ("software") stored in the memory 106. The software may include firmware, one or more applications, program data, filters, rules, one or more program modules, and other executable instructions. For example, the software may include instructions and associated data for performing the methods described herein. For example, as illustrated in FIG. 1, the memory 106 may store a triage engine 110 (for example, software) for performing patient triaging as described herein. It should be understood that the functionality described herein as being performed by the triage engine 110 may be distributed among multiple software modules, hardware components, or a combination thereof stored or included in the server 102 or external to the server 102.

The communications interface 108 allows the server 102 to communicate with devices external to the server 102. For example, as illustrated in FIG. 1, the server 102 may communicate with an image repository 112 and a cognitive system 114. In particular, the communications interface 108 may include a port for receiving a wired connection to an external device (for example, a universal serial bus (USB) cable and the like), a transceiver for establishing a wireless connection to an external device (for example, over one or more communication networks 111, such as the Internet, a local area network (LAN), a wide area network (WAN), and the like), or a combination thereof. It should be understood that FIG. 1 illustrates one example of the system 100 and, in some embodiments, the server 102 may communicate with fewer or additional systems and components than illustrated in FIG. 1. For example, the server 102 may be configured to communicate with multiple image repositories, multiple cognitive systems, or a combination thereof. Also, the systems and components illustrated in FIG. 1 may be combined and distributed in various configurations. For example, in some embodiments, the server 102 may include the image repository 112, the cognitive system 114, or a combination thereof. In some embodiments, the server 102 may also communicate with one or more user devices (terminals, tablet computers, laptop computers, desktop computers, smart wearables, smart televisions, and the like) that include similar components as the server 102. For example, in some embodiments, a user may interact with the server 102 via a user device to configure the system 100, such as by configuring or customizing the functionality of the server 102 as described herein. Although not illustrated in FIG. 1 or described herein, the image repository 112 and the cognitive system 114 may include similar components as the server 102.

The image repository 112 stores images, such as image studies. For example, in some embodiments, the image repository 112 includes a PACS. The cognitive system 114 is a computer system that applies marching learning (artificial intelligence) to mimic cognitive functions, including but not limited to learning and problem solving. Machine learning generally refers to the ability of a computer program to learn without being explicitly programmed. In some embodiments, a computer program (sometimes referred to as a learning engine) is configured to construct a model (for example, one or more algorithms) based on example inputs. Supervised learning involves presenting a computer program with example inputs and their desired (actual) outputs. The computer program is configured to learn a general rule (a model) that maps the inputs to the outputs. The computer program may be configured to perform machine learning using various types of methods and mechanisms. For example, the computer program may perform machine learning using decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using all of these approaches, a computer program may ingest, parse, and understand data and progressively refine models for data analytics. Once trained, the computer system may be referred to as an intelligent system, an artificial intelligence (AI) system, a cognitive system, or the like. Accordingly, in some embodiments, the cognitive system 114 includes Watson® provided by IBM Corporation. The cognitive system 114 may be "trained" using various machine learning techniques. In some embodiments, the cognitive system 114 may be trained using existing image studies with manually-specified classifications.

Rather than simply replicating and speeding existing human processes, computers may simultaneously process multiple tasks and draw upon multiple simultaneous information sources based on interactive rules. Therefore, unlike the human brain, which is largely a serial processor, multitasking computer system may simultaneously weigh many factors, and therefore complement or exceed human performance with regard to medical image interpretation.

As illustrated in FIG. 1, the server 102 may also communicate with a worklist system 116, a resource allocation system 118, a structured reporting system 120, a differential diagnosis system 122, or a combination thereof. The server 102 may communicate with one or more of these systems to automatically triage patients after automatically classifying an image via the cognitive system 114. Again, although not illustrated in FIG. 1 or described herein, the worklist system 116, the resource allocation system 118, the structured reporting system 120, and the differential diagnosis system 122 may include similar components as the server 102. Also, it should be understood that the functionality provided by the systems 116, 118, 120, and 122 may be combined and distributed in various configurations and, in some embodiments, one or more of these systems 116, 118, 120, and 122 may be included in the server 102, the image repository 112, the cognitive system 114, or a combination thereof.

In some embodiments, the worklist system 116 includes a PACS, a radiology information system (RIS), or a combination thereof that generates worklists (data structures) for organizing tasks of a radiologist or other physician or caregiver in the medical industry. Similarly, the resource allocation system 118 may include a hospital information system (HIS), an ordering system, such as an image study ordering system, an electronic medical record (EMR) system, or the like for reserving or ordering medical resources, including facilities, equipment, staff, and the like. The structured reporting system 120 may include a RIS that stores completed reports for image studies and, optionally, other medical reports, results, or the like. The differential diagnosis system 122 may similarly include an RIS, a HIS, an EMR, or the like configured to generate a differential diagnosis as described below.

As described in more detail below, the server 102 is configured to automatically classify image studies using the cognitive system 114. Also, after classifying and prioritizing image studies, the server 102 may take one or more automatic actions to triage or process the image studies to efficiently and effectively use medical resource.

For example, when classifying mammogram images, a radiologist typically classifies an imaging study into one of seven BI-RADS classifications: "0" requires follow-up, "1" is normal, "2" is normal with findings (lesions or cysts), "3" is unknown, "4" and "5" are high risk, and "6" is known cancer. Rather than receiving manually-determined classifications, the server 102 (via the cognitive system 114) applies one or more algorithms developed using computer vision and machine learning (AI) techniques based on deep learning methodology to classify image studies. For example, in some embodiments, the server 102 (via or independent of the cognitive system 114) is configured to 1)

detect normal and abnormal findings in imaging studies and 2) classify the patient category based on the findings. In some embodiments, the server 102 is also configured to (via or independent of the cognitive system 114) 3) compare the suspicious area to prior studies to assess change over time and 4) fuse BI-RADS estimations from multiple imaging modalities (x-ray, ultrasound, tomography, MRI, and the like) and other patient information to determine a severity of the image study (low, medium, high), which may be used a second level of classification for the image studies. In some embodiments, multiple stages of automated prioritization and classification are used, such as for screening and diagnostic imaging. For example, in breast imaging screening, one objective is to triage images that are normal and images that are not normal to identify patients who may require additional diagnostic image. Differential diagnosis may also occur during diagnostic imaging and may make use of prioritization and classification.

Accordingly, once properly trained, the cognitive system 114 can evaluate medical images (including image studies) and automatically categorize patient cases into an appropriate risk stratification or severity score rating, such as a BI-RADS classification. In some embodiments, the cognitive system 114 may use aggregated classifications of risk stratification using a known classification scheme, including the BI-RADS classification scheme. For example, BI-RADS classifications may be aggregated into four different buckets corresponding to different levels of risk: bucket "1/2" representing normal or low severity, bucket "3" representing unknown, bucket "4/5" representing abnormal or high severity, and bucket "6" representing a known cancer. In some embodiments, using buckets (an aggregate classification, such as an aggregate BI-RADS classification) may simplify the machine learning process for the cognitive system 114. In addition, in some embodiments, the position or classification of images within buckets may be organized according to chronology (first-in, first-out), randomly, or any combination of ordering systems or weights, which may be determined and modified by users or an administrator. The BI-RADS classification is used in various examples and embodiments described in the present application. However, this should not be construed as limiting and it should be understood that other types of classification schemes, including textual or numerical categories or score range (for example, a numerical score on a sliding scale between 0 and 100) may be used with the systems and methods described herein.

As also previously noted, based on the classification, the server 102 performs one or more additional automatic operations. For example, in some embodiments, the server 102 is configured to automatically generate worklists that indicate actions or operations (tasks) to be performed to treat a patient based on the automatically-set classification. In other words, using the classifications made by the cognitive system 114, the server 102 identifies high priority or severity cases (high risk cases) and, for each identified case, generates a corresponding worklist detailing the subsequent operations that need to be performed to treat the patient. The generated worklist may include actions such as scheduling a room to perform a biopsy done, returning results to the patient, and the like. The server 102 may communicate with the worklist system 116 to automatically generate one or more worklists.

The server 102 may also be configured to automatically take one or more actions based on the generated worklist, the classification set for a case, or a combination thereof. For example, the server 102 may be configured to route medical imaging studies to a particular radiologist. As one example, the server 102 may be configured to route higher priority cases identified from mammogram images, which may be complex, to a specialized breast radiologist who has more experience with complex cases. Similarly, the server 102 may route lower priority cases to a staff radiologist (non-specialist) to confirm the initial automatic classification for the study. This automatic and intelligent routing of image studies allows for the prioritization of the workflow for a particular person (radiologist) to view the medical images of the patient based on the initial automated triage of the patient.

In addition or alternatively, the server 102 may be configured to automatically reserve medical resources for treatment of a patient based on the triage of the patient and the automated cognitive classification of the patient's case. For example, the server 102 may interface with the resource allocation system 118 (a HIS) to automatically reserve hospital staff, facilities, equipment, or a combination thereof to treat the patient based on the priority of the patient's case. As one example, the server 102 may be configured to interface with the resource allocation system 118 to automatically pre-schedule a biopsy for a patient and reserve associated hospital resources for performing the biopsy. This reservation or allocation may feed other systems, such as hospital/lab resource scheduling and allocation systems.

In addition or alternatively, the server 102 may be configured to generate and output a report, including a structured medical report commonly created by a radiologist after evaluating an image study. For example, in some embodiments, the server 102 may generate and output a report for lower priority cases, including cases classified as "normal." Alternatively or in addition, the server 102 may be configured to generate and output a report for other classifications, including cases classified as not "normal." The generated report may indicate the classification of the patient's case determined by the system. The server 102 may interface with the structured reporting system 120 to generate the report and forward the generated report to a radiologist for review and approve (signature). Similarly, in some embodiments, the cognitive system 114 may be used as a double check of a radiologist's evaluation of the medical images. For example, when a radiologist provides input that a patient's case is classified as "normal," this input can be fed into the cognitive system 114, which can verify that the patient's medical images do in fact appear to represent a "normal" case. In response to the cognitive system 114 determining that radiologist's input may be incorrect (the cognitive system 114 determines a different classification), the server 102 may generate a notification or flag and may prompt the radiologist to confirm his or her input, indicate a reason for the input, change his or her input, or a combination thereof. This input from the radiologist may be used by the cognitive system 114 to update the model using machine learning.

In addition or alternatively, the server 102 may be configured to provide a differential diagnosis. In the medical industry, a differential diagnosis is the distinguishing of a particular disease or condition from others that present similar clinical features. Accordingly, the server 102 may be configured to interface with the differential diagnosis system 122 to automatically perform differential diagnostic procedures to diagnose a specific disease or condition in a patient or, at least, to eliminate one or more diseases, such as imminently life-threatening diseases or conditions. In some embodiments, each individual option of a possible disease is called a "differential diagnosis." For example, the condition "acute bronchitis" could be a differential diagnosis in the evaluation of a cough that ends up with a final diagnosis of a common cold. In some embodiments, the server 102 may present each differential diagnosis with a probability, such as a "high" probability of cancer or a "low" probability of cancer. Accordingly, the server may automatically compare the results of analyzing the medical images to other clinical data, such as patient electronic medical record (EMR) data, to determine or rule out certain diagnoses or conditions. The server 102 may be configured to populate a report with a differential diagnosis, transmit a differential diagnosis to another system (a hospital system, a messaging or communication system, or the like), or a combination thereof. The server 102 may also be configured to automatically triaging (including adjusting or modifying previous triaging) of the image study based on the differential diagnosis. For example, automated AI-based differential diagnosis can influence worklist prioritization. In particular, if a change is detected since the last exam or a suspicious lesion is detected, the cognitive system 114 may be configured to automatically change a worklist priority for a reader, create alerts or warnings, schedule resources, or the like.

Figure 2:
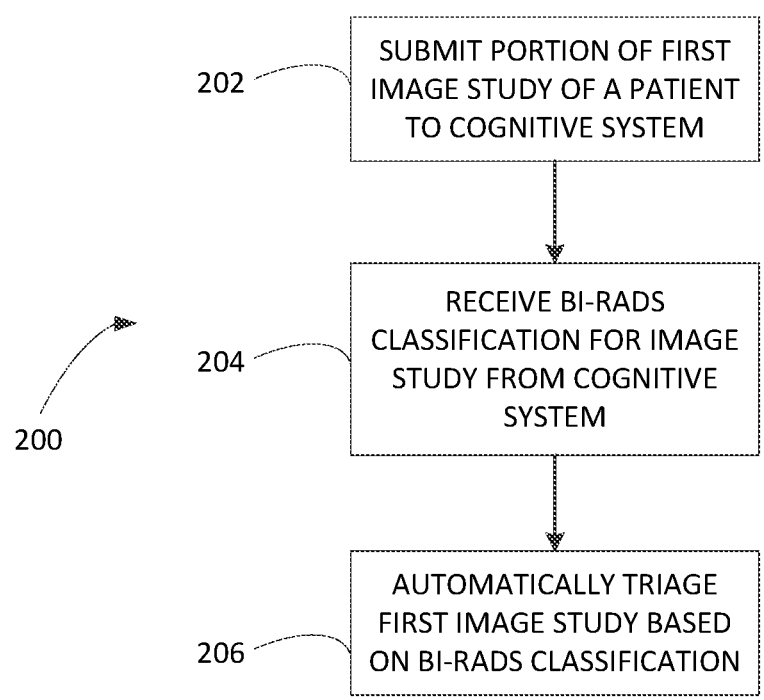
FIG. 2 is a flowchart illustrating a method of automatically triaging image studies using the system of FIG. 1 according to some embodiments.

For example, FIG. 2 illustrates a method 200 performed by the server 102 (the electronic processor 104 executing instructions, such as the triage engine 110) for automatically triaging image studies according to some embodiments. The method 200 is described with respect to image studies captured as part of a breast cancer screening process and performing classifications via the BI-RADS classification scheme. However, this process is used as an example and should not be considered as limiting. As noted above, breast cancer screening is typically performed in a two-step process, and radiologists review the image studies captured as part of a first step of the process to determine what patients should have additional screening. Accordingly, as described below, the server 102 may be configured to automatically triage these initial image studies to determine what patients should undergo the second screening.

As illustrated in FIG. 2, the method 200 includes submitting, with the server 102, at least a portion of an image study of a patient generated as part of a medical imaging procedure to the cognitive system 114 (at block 202). In some embodiments, the server 102 initially receives the image study from the image repository 112 and submits the image study (or a portion thereof) to the cognitive system 114. In other embodiments, the server 102 submits the image study (or a portion thereof) to the cognitive system 114 by providing the cognitive system 114 with an identifier for accessing the image study, such as via the image repository 112. As described above, the cognitive system 114 is configured to analyze the image study using a model developed using machine learning. Accordingly, the method 200 also includes receiving, from the cognitive system, a BI-RADS classification assigned to the image study using the model (at block 206). As noted above, in some embodiments, the BI-RADS classification includes an aggregate BI-RADS classification (a bucket representing different levels or groups of classifications).

As illustrated in FIG. 2, the server 102 automatically triages the image study based on the classification assigned to the image study by the cognitive system 114 (at block 206). For example, as noted above, based on the BI-RADS classification, the image study is triaged by identifying whether the patient needs to return for the second phase of breast cancer screening. In particular, the server 102 may be configured to assign a severity classification to the image study based on the BI-RADS classification assigned by the cognitive system 114 to triage the image study. The severity classification may specify whether additional screening is necessary and potentially an urgency of the additional screening. In some embodiments, the server 102 also sets the severity classification based on data in addition to the BI-RADS classification assigned by the cognitive system 114. For example, the server 102 may be configured to assign the severity classification by comparing an image included in the image study with an image included in a prior image study for the patient. When the server 102 compares the image in the image study with the image included in the prior image study, the server 102 is configured to determine a patient change between the image study and the prior image study.

Similarly, the server 102 may be configured to assign the severity classification by comparing a BI-RADS classification of the image with the BI-RADS classification for another image study of the patient. For example, the other image study of the patient may be an image study that was taken in a different image modality than the original image study (for example, the original image study may include an x-ray image, while the other image study may include a CT scan image). The server 102 may be configured to automatically triage the image study based on the BI-RADS classification of the image study, the patient change as described above, and the BI-RADS classification assigned to the other image study of the patient. For example, discrepancies based on differences between severity scores seen on different modalities could trigger changes to worklist prioritization and other actions as described herein.

In some embodiments, before the image study is submitted to the cognitive system 114, the image study may be provided a first BI-RADS classification manually by a radiologist. The server 102 may then submit at least a portion of the image study to cognitive system 114 (as in block 202) and receive a second BI-RADS classification back from the cognitive system 114 (as in block 204). The server 102 then compares the first BI-RADS classification to the second BI-RADS classification to determine if the classifications differ. If the classifications differ, the server 102 may be configured to generate an alert for the radiologist to confirm the first BI-RADS classification made by the radiologist. If the server 102 receives input from the radiologist confirming the first BI-RADS classification, the server 102 may provide the first BI-RADS classification to the cognitive system 114 as feedback for updating the model using machine learning. Further details and options regarding using the cognitive system 114 as a double check of manually-generated classifications, reports, or diagnosis are provided below with respect to FIG. 7.

Figure 3:
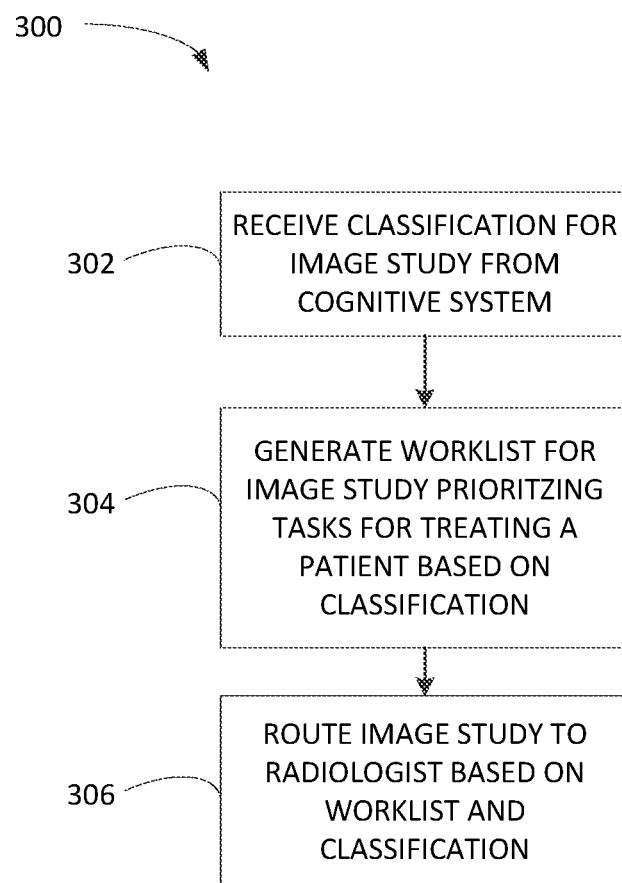
FIG. 3 is a flowchart illustrating a method of automatically generating a worklist using the system of FIG. 1 according to some embodiments.

As noted above, the triaging an image study based on an automated classification may include taking one or more automatic actions. For example, FIG. 3 is a flowchart illustrating a method 300 of automatically generating a worklist using the system 100 according to some embodiments, which may be performed as part of triaging an image study. As illustrated in FIG. 3, the method 300 includes receiving, with the server 102, a BI-RADS classification for an image study from the cognitive system 114 (at block 302) as described above with respect to FIG. 2.

As also shown in FIG. 3, the method 300 further includes generating, with the server 102, a worklist for the image study that prioritizes tasks for treating a patient based on the BI-RADS classification (at block 304). For example, if the BI-RADS classification of the image study is a "5" (highly suspicious), the server 102 may generate a list of tasks that include a plan for a biopsy procedure. If the BI-RADs classification of the image study is "4" (suspicious), the server 102 may generate a list of tasks that include a series of different scans to produce new images to confirm that cancer is present. In another embodiment, the list of tasks for different BI-RADS classifications (for example, "4" and "5") may be the same list, but the tasks may be prioritized in a different order based on the BI-RADS classification. For example, if the BI-RADS classification is a "5" (highly suspicious), the server 102 may prioritize a task for determining an appropriate biopsy for a patient over a task for scheduling different imaging exams.

The method 300 also includes routing, with the server 102, the image study to a radiologist based on the worklist and the BI-RADS classification (at block 306). For example, if the BI-RADS classification is a "5" (highly suspicious) and the worklist includes a prioritized task for "perform MRI scan," the server 102 may route the image study to a radiologist whose specialty is magnetic resonance imaging (MRI). In another embodiment, if the BI-RADS classification is a "0" (requires follow-up) and the worklist includes a prioritized task to "determine further image studies," the server 102 may route the image study to a radiologist who can further analyze the image study to determine what other types of image studies should be performed. The server 102 may be configured to route the image study to multiple radiologists (in some embodiments, in a specific order) to handle different tasks.

Figure 4:
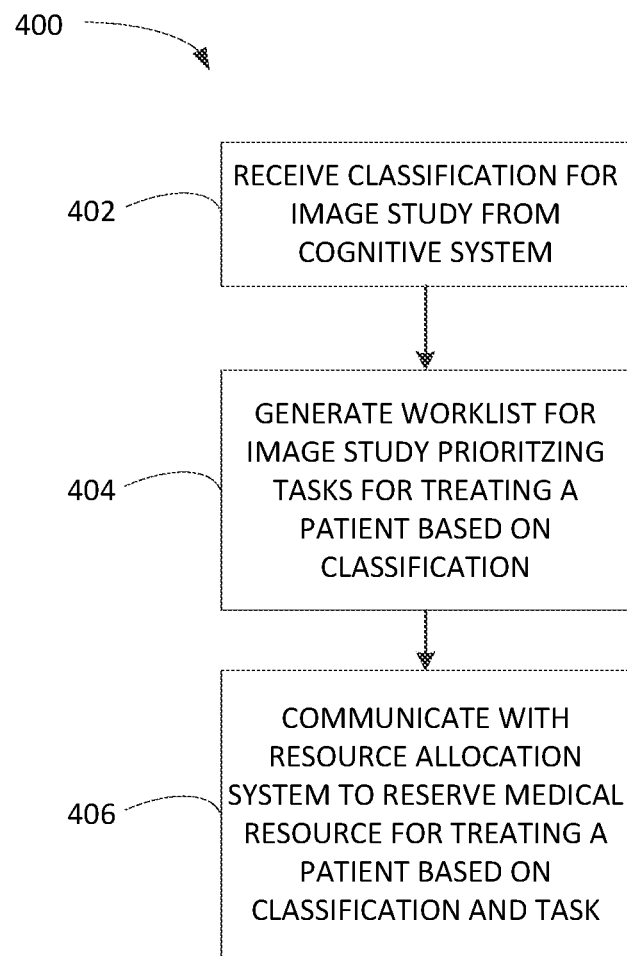
FIG. 4 is a flowchart illustrating a method of automatically reserving medical resources using the system of FIG. 1 according to some embodiments.

In addition to or as an alternative to automatically generating a prioritized worklist, the server 102 may be configured to automatically reserve medical resources. For example, FIG. 4 is a flowchart illustrating a method 400 of automatically reserving medical resources using the system 100 according to some embodiments, which may be performed as part of triaging an image study. The method 400 includes receiving, with the server 102, a BI-RADS classification for an image study from the cognitive system 114 (at block 402) as described above with respect to FIG. 2. As illustrated in FIG. 4, the method may also include generating, with the server 102, a worklist prioritizing tasks for treating a patient based on the BI-RADS classification (at block 404) as described above with respect to FIG. 3. As noted above, BI-RADS classifications are provided as one example and the method 400 may be used with other types of classifications or scoring mechanisms.

The method 400 includes communicating, using the server 102, with the resource allocation system 118 to reserve medical resources for treating a patient based on a BI-RADS classification of the image study and a task included in the worklist (at block 406). For example, if the server 102 receives a BI-RADS classification of "5" (highly suspicious) and a task includes "schedule biopsy," the server 102 may communicate with the resource allocation system 118 to reserve time with a technician, reserve a room in a medical facility, and the like. In another embodiment, if the BI-RADS classification is a "4" (suspicious) and tasks include a series of different image scans to be taken, the server 102 may communicate with the resource allocation system 118 to schedule each of the necessary images. In some embodiments, the server 102 may allow for a radiologist or a patient to have input into the communication with the resource allocation system 118. For example, the server 102 may return a plurality of times for a scan, a plurality of locations for a scan, and a plurality of radiologists who can perform a scan, and prompt the patient or the radiologist to select a time, location, or radiologists.

Figure 5:
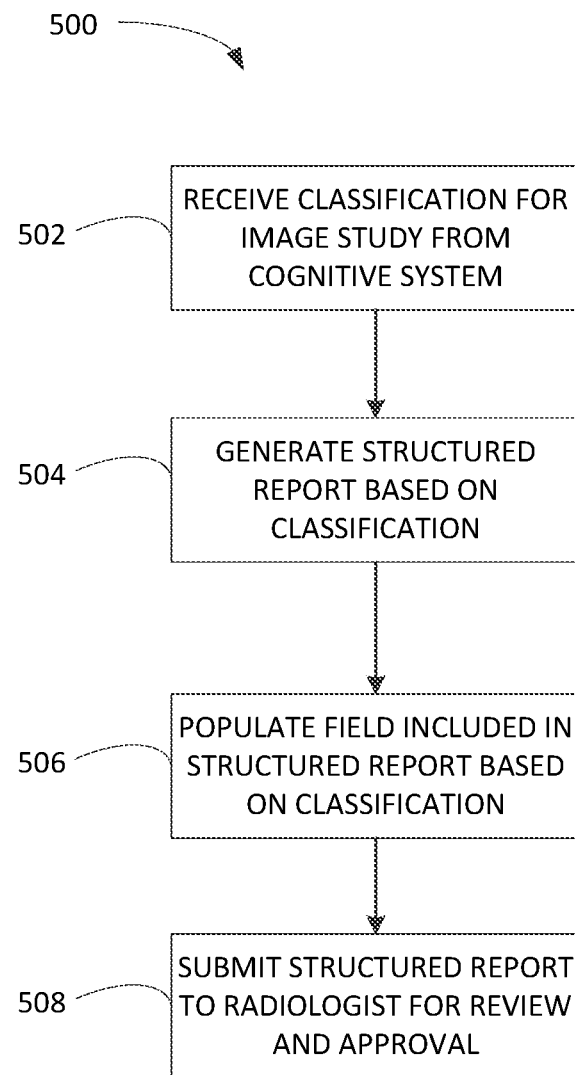
FIG. 5 is a flowchart illustrating a method of automatically generating a structured medical report using the system of FIG. 1 according to some embodiments.

In addition to or as an alternative to automatically generating a prioritized worklist, reserving resources, or a combination thereof, the server 102 may be configured to automatically generate a report for the image study, such as a structured medical report. For example, FIG. 5 is a flowchart illustrating a method 500 of automatically generating a structured medical report using the system 100 according to some embodiments, which may be performed as part of triaging an image study. As illustrated in FIG. 5, the method 500 includes receiving, with the server 102, a BI-RADS classification for an image study from the cognitive system 114 (at block 502) as described above with respect to FIG. 2. Again, as noted above, BI-RADS classifications are provided as one example and the method 500 may be used with other types of classifications or scoring mechanisms.

The method 500 also includes generating, using the server 102, a structured report based on the BI-RADS classification (at block 504). The server 102 may interact with the structured reporting system 120 to generate the structured report. The structured report may be similar to a structured report that would be created by a radiologist after an evaluation of an image study. In some embodiments, the server 102 is configured to only generate a portion of a structured report. For example, if the image study is concerned with a mass in a breast, the portion of the report may only be concerned with specific types of masses or only with images of a breast of the patient.

The method 500 further includes populating, using the server 102, a field in the structured report based on the BI-RADS classification (at block 506). For example, if the BI-RADS classification is a "5" (highly suspicious), the server 102 may populate a field ("Mass is Cancerous?") with a "true" value. The server 102 may also be configured to populate a field with the BI-RADS classification. In addition, the server 102 may be configured to calculate a quantitative value (such as a size of a mass) and populate the field with the quantitative value.

The method 500 also includes submitting, using the server 102, the structured report generated at block 504 with the field populated at block 506 to a radiologist for review and approval (at block 508). The radiologist confirms that the structured report is accurate and that the populated field contains the correct value. The radiologist may add or change values to fields in the structured report as part of the review and approval process. In some embodiments, the radiologist may include more fields that were not initially generated with the report.

Figure 6:
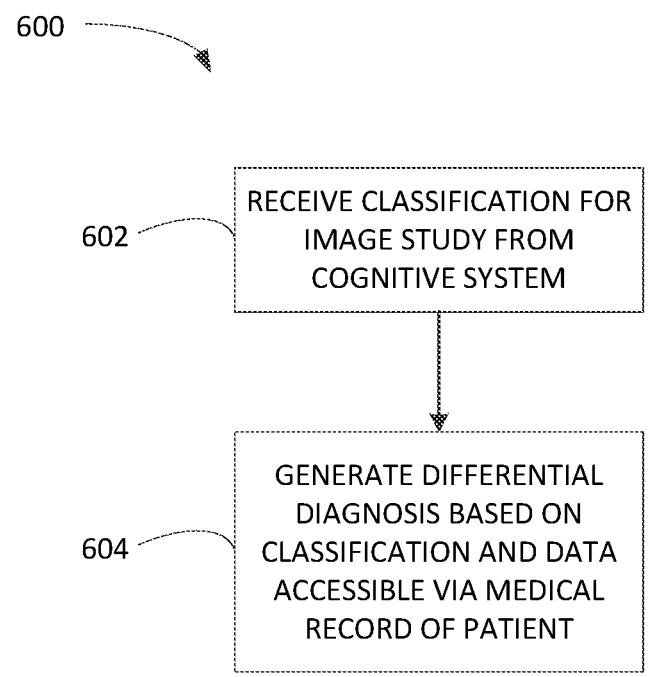
FIG. 6 is a flowchart illustrating a method of automatically generating a differential diagnosis using the system of FIG. 1 according to some embodiments.

In addition to or as an alternative to automatically generating a prioritized worklist, reserving resources, generating a report, or a combination thereof, the server 102 may be configured to automatically generate a differential diagnosis. For example, FIG. 6 is a flowchart illustrating a method 600 of automatically generating a differential diagnosis using the system 100 according to some embodiments, which may be performed as part of triaging an image study. As illustrated in FIG. 6, the method 600 includes receiving, using the server 102, a BI-RADS classification for an image study from the cognitive system 114 (at block 602), similar to block 204 of the method 200 as described above. Again, as noted above, BI-RADS classifications are provided as one example and the method 600 may be used with other types of classifications or scoring mechanisms.

The method 600 includes generating, with the server 102, a differential diagnosis based on the BI-RADS classification and data accessible via medical records of the patient (at block 604). As described above, a differential diagnosis may rule out particular diseases or conditions, may assign a probability to particular diseases or conditions, or a combination thereof. The server 102 may access patient data (separate from the image study) to perform the differential diagnosis. For example, the server 102 may be configured to access patient data through an electronic medical record of the patient. Accordingly, the server 102 may be configured to rule out particular diagnoses (diseases, conditions, findings, and the like) by looking at laboratory results, treatments, prescriptions, other imaging results, patient history (including family history), patient demographics, and the like. In some embodiments, the server 102 updates the original BI-RADS classification based on the results of the differential diagnosis. In other embodiments, the server 102 may provide (display) the differential diagnosis to a user to aid the user in confirming a diagnosis for the patient. The differential diagnosis can also be used to determine various automated actions to take to triage the patient as described above. For example, the results of the differential diagnosis may be used to determine and prioritize worklist tasks, reserve medical resources, generate a structured report, and the like.

The automated actions described above to classify triage a particular patient may be applied based on various rules or user preferences. For example, the server 102 may be configured to apply one or more rules that define preferences. The rules may be associated with a patient, a facility, a radiologist, a network, a geographical area, a type of imaging modality, or the like. Accordingly, the server 102 may be configured to take a particular action through application of the rules, wherein the actions vary based on the patient, the facility, a radiologist, a network, a geographical area, a type of imaging modality, or the like. For example, a particular radiologist may want a structured report generated for all classifications or may prefer a particular order of tasks in a worklist for particular classification. These rules can be manually set or configured or can be set or modified using machine learning. For example, if a radiologist always reorders tasks in a worklist, the server 102 may be configured to automatically set a rule for the radiologist that sets the required task order.

As noted above, the cognitive system 114 may be used to initially classify images or as a double-check for manual classifications. For example, incorporating artificial intelligence into a medical system is challenging. As with humans, artificial intelligence will not be perfect. Thus, if the cognitive system 114 shows an analysis of a case before a medical professional has read the case, the medical professional's ultimate diagnosis may be influenced by the automated analysis.

Accordingly, the cognitive system 114 and other forms of artificial intelligence can be used to perform a double check or a "second read" that checks the results of a medical professional. For example, the cognitive system 114 can be used as a backend or background process that automatically analyzes medical images. The initial reading physician may not have access to the automatic analysis. However, after a reading physician submits a manual analysis for a particular image, the server 102 may be configured to detect whether there is a discrepancy between the cognitive system's conclusion (classification) and the medical professional's conclusion (classification). In response to detecting a discrepancy, the server 102 may be configured to automatically route the medical image to another medical professional for review (an adjudicating radiologist). In some embodiments, the adjudicating radiologist is not permitted to access the original medical professional's conclusion or the automatic conclusion, which allows the adjudicating radiologist to make an independent diagnosis.

Various rules (including user preferences, patient preferences, radiologist preferences, and the like as described above) can be applied that determine what conclusion is used as the ultimate conclusion. For example, when the manual conclusion and the automatic conclusion agree, the manual conclusion (manually-generated report) may be submitted as the final conclusion for the medical image. However, in other embodiments, the automatic conclusion or both conclusions may be submitted as the final conclusion. Similarly, when the manual conclusion and the automatic conclusion do not agree, the conclusion from the adjudicating radiologist may be used the final conclusion (regardless of whether the adjudicating radiologist's conclusion agree with either of the manual conclusion or the automatic conclusion. Alternatively, the conclusion from the adjudicating radiologist may be compared with the manual conclusion, the automatic conclusion, or both before a final conclusion is submitted. For example, when the adjudicating radiologist's conclusion agrees with the manual conclusion, the manual conclusion, the adjudicating radiologist's conclusion, or a common diagnostic result between the conclusions may be submitted. Submitting a conclusion may include submission of a generated report with at least one finding or diagnosis, such as to a RIS, a PACS, or the like. Alternatively, when the adjudicating radiologist's conclusion does not agree with the manual conclusion, the automated conclusion may be used or another conclusion may be solicited from another adjudicating radiologist, whose conclusion may be considered as the final conclusion.

Also, if the adjudicating radiologist does not side with the automatic conclusion, the image or images being reviewed by the adjudicating radiologist may be submitted to a machine learning algorithm used by the cognitive system 114. This feedback loop helps train the cognitive system 114 to improve over time toward consistency with human interpretation.

Figure 7:
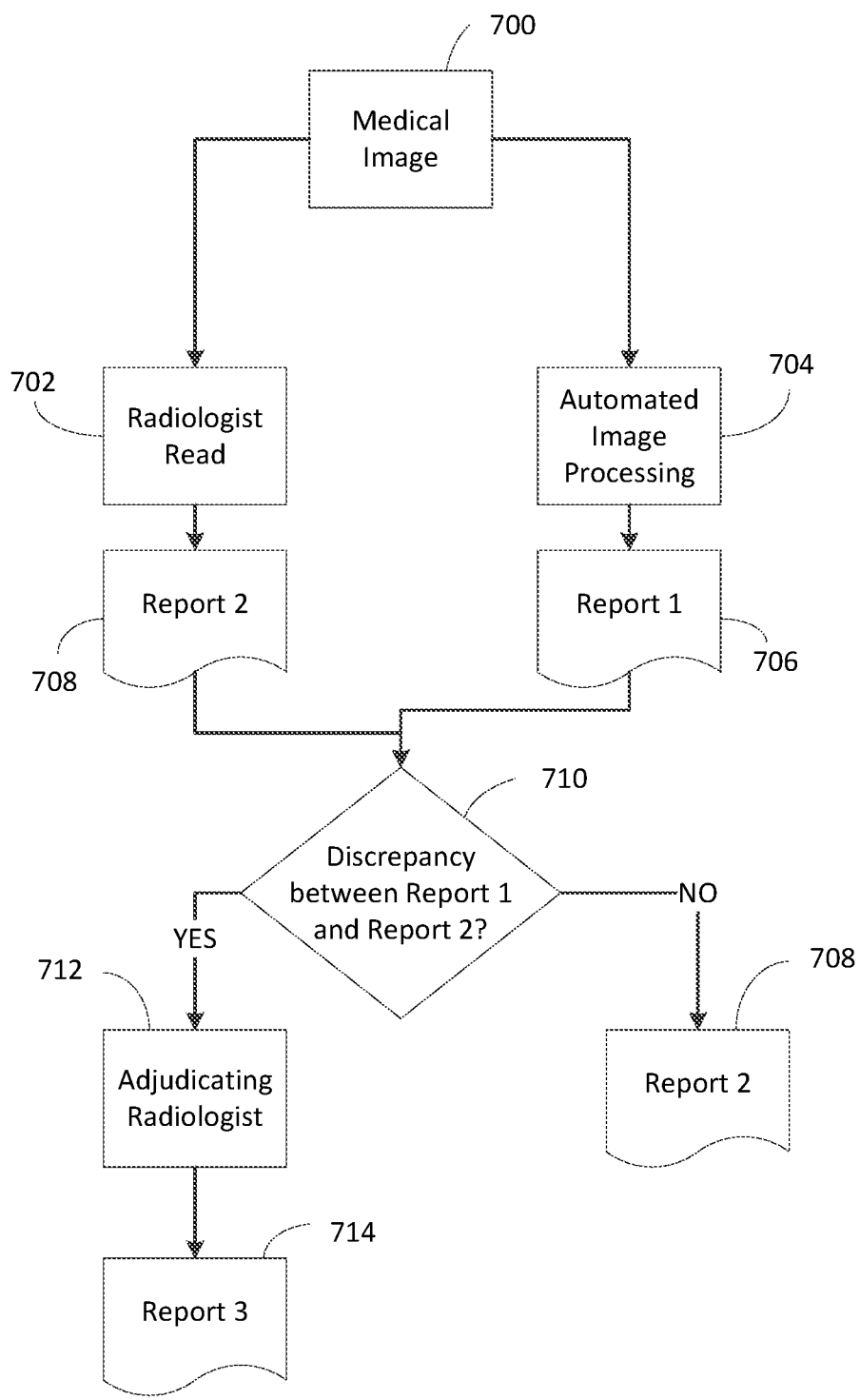
FIG. 7 schematically illustrates an automated process for handling discrepancies between a human-generated report or diagnosis and a diagnosis generated by the system of FIG. 1 according to some embodiments.

For example, as illustrated in FIG. 7, a medical image 700 arrives (from an imaging modality) and is sent both to a radiologist 702 to read on a medical image viewer (for example, a PACS viewer) and to a cognitive system 704, such as the system 114. The cognitive system 704 generates a first report 706, and the radiologist 702 generates a second report 708. The server 102 (at 710) then determines whether there is a discrepancy between the first report 706 and the second report 708. If there no discrepancy (or no major discrepancy), the second report 708 may be submitted for the medical image 700. However, if there is a discrepancy, the medical image 700 is routed to an adjudicating radiologist 712 (different from the radiologist 702), who generates a third repot 714 that may be submitted for the medical image.

Thus, embodiments described herein provide methods and systems for automatically classifying image studies and automatically triaging the image study based on the classification.

Various features and advantages of the invention are set forth in the following claims.

What is claimed is:

1. A system for verifying a manually-generated report for a medical image, the system comprising:
   an electronic processor configured to
   receive a first report for the medical image generated by a first radiologist,
   receive a second report for the medical image generated by a cognitive system, automatically compare the first report and the second report to detect a discrepancy between the first report and the second report, in response to not detecting a discrepancy between the first report and the second report, submitting the first report for the medical image, in response to detecting a discrepancy between the first report and the second report, assign the medical image to a second radiologist, receive a third report for the medical image generated by the second radiologist, and select from the first report, second report, and third report, a selected report by applying at least one rule to determine whether to submit the first report, the second report, or the third report for the medical image, the at least one rule associated with at least one selected from a group consisting of a patient a facility, a radiologist a network, a geographical area, and a type of imaging modality, and submit the selected report.

2. The system of claim 1, wherein the first radiologist does not have access to the second report.

3. The system of claim 1, wherein the second radiologist does not have access to the first report.

4. The system of claim 1, wherein the first report includes a first BI-RADS classification and the second report includes a second BI-RADS classification and wherein the electronic processor is configured to compare the first report and the second report by determining whether the first BI-RADS classification is different than the second BI-RADS classification.

5. The system of claim 1, wherein the electronic processor is further configured to compare the third report and the first report and wherein the electronic processor is configured to apply at least one rule to determine whether to submit the first report, the second report, or the third report for the medical image in response to the third report and the first report not having a discrepancy.

6. The system of claim 5, wherein the electronic processor is further configured to assign the medical image to a third radiologist in response to the third report and the first report having a discrepancy.

7. A method for verifying a manually-generated report for a medical image, the method comprising:

receiving, with an electronic processor, a first report for the medical image generated by a first radiologist;

receiving, with the electronic processor, a second report for the medical image generated by a cognitive system, wherein the first report is generated without access to the second report;

automatically, with the electronic processor, comparing the first report and the second report to detect a discrepancy between the first report and the second report;

in response to not detecting a discrepancy between the first report and the second report, automatically submitting, with the electronic processor, the first report for the medical image, in response to detecting a discrepancy between the first report and the second report, assigning the medical image to a second radiologist, receiving a third report for the medical image generated by the second radiologist, and selecting, from the first report, the second report, and the third report, a selected report by applying at least one rule to determine whether to submit the first report, the second report, or the third report for the medical image, the at least one rule associated with at least one selected from a group consisting of a patient, a facility, a radiologist, a network, a geographical area, and a type of imaging modality, and submitting the selected report.

8. The method of claim 7, wherein assigning the medical image to the second radiologist includes assigning the medical image to the second radiologist for completion of the third report without access to the first report and the second report.

9. The method of claim 7, wherein receiving the first report includes receiving a first BI-RADS classification, wherein receiving the second report includes receiving a second BI-RADS classification, and wherein comparing the first report and the second report includes determining whether the first BI-RADS classification is different than the second BI-RADS classification.

10. The method of claim 7, further comprising comparing the third report and the first report and wherein applying at least one rule to determine whether to submit the first report, the second report, or the third report for the medical image further includes submitting the third report in response to the third report and the first report not having a discrepancy.

11. The method of claim 10, further comprising assigning the medical image to a third radiologist in response to the third report and the first report having a discrepancy.

12. The method of claim 7, further comprising developing the at least one rule using machine learning.

13. Non-transitory computer readable medium storing instructions that, when executed by an electronic processor, perform a set of functions, the set of functions comprising:

receiving a first report for the medical image generated by a first radiologist;

receiving a second report for the medical image generated by a cognitive system, wherein the first report is generated without access to the second report;

automatically comparing the first report and the second report to detect a discrepancy between the first report and the second report;

in response to not detecting a discrepancy between the first report and the second report, automatically submitting at least one of the first report and the second report for the medical image, in response to detecting a discrepancy between the first report and the second report, assigning the medical image to a second radiologist for completion of a third report without access to the first report and the second report, receiving a third report for the medical image generated by the second radiologist, and selecting, from the first report, the second report, and the third report, a selected report by applying at least one rule to determine whether to submit the first report, the second report, or the third report for the medical image, the at least one rule associated with at least one selected from a group consisting of a patient, a facility, a radiologist, a network, a geographical area, and a type of imaging modality; and submitting the selected report.

14. The computer readable medium of claim 13, wherein receiving the first report includes receiving a first BI-RADS classification, wherein receiving the second report includes receiving a second BI-RADS classification, and wherein comparing the first report and the second report includes determining whether the first BI-RADS classification is different than the second BI-RADS classification.

15. The computer-readable medium of claim 13, the set of functions further comprising comparing the third report and the first report and wherein submitting the third report for the medical image includes submitting the third report in response to the third report and the first report not having a discrepancy.

16. The computer-readable medium of claim 15, the set of functions further comprising assigning the medical image to a third radiologist in response to the third report and the first report having a discrepancy.

17. The computer-readable medium of claim 15, wherein the at least one rule is developed using machine learning.

* * * * *